United States Patent [19]
Nicolaou et al.

[11] Patent Number: 5,750,691
[45] Date of Patent: May 12, 1998

[54] ACCESS TO TAXOL ANALOGS

[75] Inventors: K. C. Nicolaou, La Jolla; Philippe G. Nantermet, San Diego; Rodney K. Guy, San Diego; Hiroaki Ueno, San Diego, all of Calif.

[73] Assignee: The Scripps Research Institute, La Jolla, Calif.

[21] Appl. No.: 512,229

[22] Filed: Aug. 7, 1995

Related U.S. Application Data

[62] Division of Ser. No. 110,095, Aug. 20, 1993, Pat. No. 5,440,057.

[51] Int. Cl.$^6$ .............. C07D 239/10; C07D 217/24; C07D 411/06; C07D 333/18
[52] U.S. Cl. .............. 544/238; 544/335; 546/147; 546/165; 548/454; 548/525; 549/23; 549/57; 549/60
[58] Field of Search .............. 544/238, 335; 546/147, 165; 548/454, 525; 549/23, 57, 60

[56] References Cited

U.S. PATENT DOCUMENTS 5,274,124  12/1993  Holton .............. 549/215

OTHER PUBLICATIONS

Nicolaou, et al., "Convergent Strategy Towards Taxol. A Facile Enantioselective Entry Into A Fully Functionalized Ring A System", *J. Chem. Soc., Chem. Commun.*, 1117–1118 (1992).

Nicolaou, et al., "Synthesis of a Fully Functionalized CD Ring System of Taxol", *J. Chem. Soc., Chem. Commun.*, 1118–1119 (1992).

Nicolaou, et al., "Synthesis of ABC Taxoid Ring Systems via a Convergent Strategy", *J. Chem. Soc., Chem. Commun.*, 1024–1026 (1993).

Nicolaou, et al., "Design, Synthesis and Biological Activity of Protaxols", *Nature*, 364: 464–467 (1993).

Ojima, et al., "New and Effective Approaches to the Semi-synthesis of Taxol and its C–13 Side Chain Analogs by Means of B–Lactam Synthon Method", *Tetrahedron*, 48: 6985–7012 (1992).

Ojima, et al., "A Highly Efficient Route to Taxotere by the B–Lactam Synthon Method", *Tet. Letters*, 34: 4149–4152 (1993).

Holton, R., "Method for Preparation of Taxol", *Chem. Abstracts*, 114: 164568q (1990).

Griffith, et al., "TPAP: Tetra–n–propylammonium Perruthenate, A Mild and Convenient Oxidant for Alcohols", *Aldrichimica Acta*, 23: 13–19 (1990).

*Primary Examiner*—Johann Richter
*Assistant Examiner*—Ebenezer Sackey
*Attorney, Agent, or Firm*—Donald G. Lewis

[57] ABSTRACT

Transformations of taxol, baccatin III and of 10-deacetyl baccatin III provide access to novel taxol analogs and key intermediates thereto.

2 Claims, No Drawings

ACCESS TO TAXOL ANALOGS

This is a divisional of application Ser. No. 08/110,095, filed Aug. 20, 1993 whose disclosures are incorporated herein by reference now U.S. Pat. No. 5,440,057.

FIELD OF INVENTION

The invention relates to taxol and to the synthesis of taxol analogs. More particularly, the invention relates to processes and key intermediates for synthesizing taxol analogs.

BACKGROUND

Taxol is a natural product with anti-cancer activity. Because natural sources of taxol are limited, synthetic methods for producing taxol have been developed, e.g., K. C. Nicolaou et al., *J. Chem. Soc., Chem. Commun.* 1992, 1117–1118, *J. Chem. Soc., Chem. Commun.* 1992, 1118–1120, and *J. Chem. Soc., Chem. Commun.* 1993, 1024–1026. Several synthetic taxol analogs have also been developed and have been found to have altered chemical and biological activity as compared to natural taxol, e.g., K. C. Nicolaou et al., *Nature*, 1993, 364, 464–466. There is considerable interest in the design and production of further taxol analogs. However, progress with respect to the synthesis of such taxol analogs has been blocked by a lack of information regarding certain key synthetic methods and key intermediates essential for the production of a wide range of taxol analogs.

What is needed is the identification of key synthetic methods and key intermediates for producing taxol analogs having altered activities.

SUMMARY

Novel transformations of taxol, baccatin III and of 10-deacetyl baccatin III are disclosed. These transformations and key intermediates provide access to novel taxol analogs.

DETAILED DESCRIPTION

We disclose herein degradative studies of the natural taxol product. Our objectives are bipartite: we provide first hand knowledge about the chemistry of those compounds arising late in our synthetic plan (supra) and we also provide access to the synthesis of derivatives which have not been previously explored.

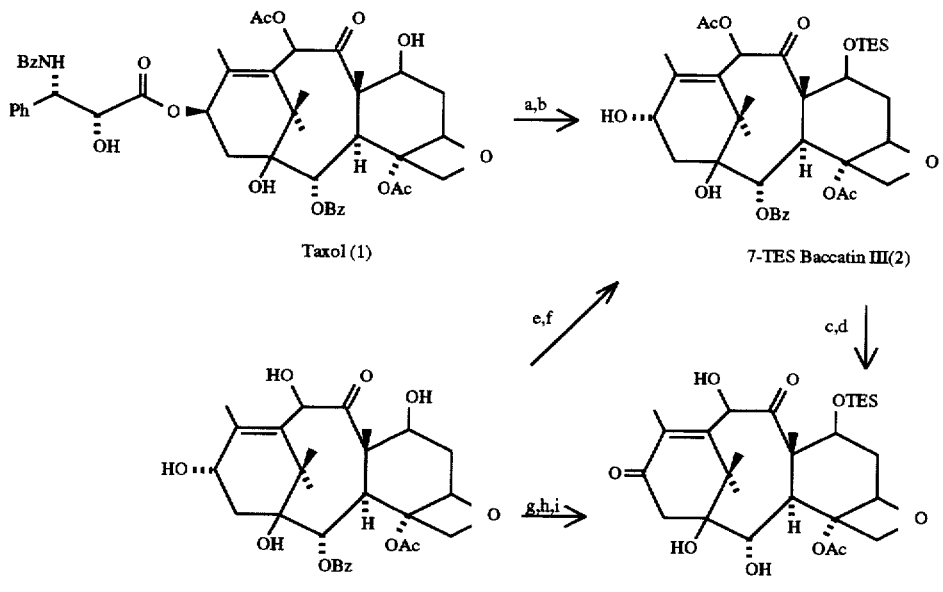

Scheme 1:
Interconversion of the natural products and synthesis of the common enone triol 4.

Taxol (1)

7-TES Baccatin III (2)

10-deacetyl Baccatin III (3)

4

Reagents and conditions:
(a) nBu$_4$NHB$_4$ (5 eq.), CH$_2$Cl$_2$, 25° C., 20 h, 77%;
(b) TESCl (20 eq.), pyridine, 25° C., 20 h, 77%;
(c) TPAP (0.05 eq.), NMO (1.5 eq.), 4 A sieves, CH$_2$Cl$_2$, 25° C., 30 min., 98%
(d) K$_2$CO$_3$ (0.05 eq.), MeOH:H$_2$O, 0° C., 6 h, 81% (5:1 mixture);
(e) TESCl (20 eq.), pyridine, 25° C., 20 h, 89%;
(f) AcCl (5 eq.), pyridine, 25° C., 20 h, 77%;
(g) TESCl (20 eq.), pyridine, 25° C., 23 h, 89%;
(h) TPAP (0.05 eq.), NMO (1.5 eq.) 4 A sieves, CH$_2$Cl$_2$, 25° C., 30 min., 80%;
(i) K$_2$CO$_3$ (0.05) eq.), MeOH:H$_2$O, 0° C., 3 h, 92% (5:1 mixture).
{Ac = acetyl; TES = triethylsilyl; TPAP = tetra-n-propylammoniumperruthenate; NMO = N-methylmorpholine-N-oxide}.

Our initial goal was to produce a C1–C2 vicinal diol that could be used to explore benzylation of the C2 hydroxyl group, a process that we considered crucial to the success of our synthetic endeavors. Towards this end, reductive deesterification of taxol (1) followed by selective silylation of the C7 hydroxyl group with triethyl silyl chloride (TES-Cl) produced, as per literature precedent (Nicolaou, supra; N. F. Magri et al., *Journal of Organic Chemistry* 1986: vol. 51, pages 3239–3242; and J. -N. Denis et al., *Journal of the American Chemical Society* 1988vol. 110, pages 5917–5919), 7-TES Baccatin III (2) (Scheme 1). All attempts to selectively deprotect the C2 and C10 positions, including both metal hydride reduction and basic hydrolysis, produced a mixture containing completely deesterified materials and rearranged products giving extremely low (15–30%) yields of the desired compound 4, a result which is in accordance with other groups result's. We hypothesized that oxidation of the C13 hydroxyl group would remove a suspected hydrogen bond between this hydroxyl group and the C4 acetoxy group thus rendering the acetyl group less susceptible to both nucleophillic deprotection processes. Indeed, catalytic oxidation with Ley's ruthenium system gave the C13 ketone that was readily hydrolyzed under basic conditions to provide a single product, 4, in high yield. Subsequently, we found that this material could be easily produced from all three of the commonly available taxoid natural products: taxol, baccatin III, and 10-deacetylbaccatin III. This enone triol 4 gave a convenient starting point for all of our further studies.

During our preliminary survey of methods for selectively introducing the C2 benzoyl group, we envisaged the possibility of directly converting a C1–C2 carbonate into a C2 benzoate by the simple addition of a nucleophillic phenyl reagent. This method would provide a double role to the carbonate: first as a convenient protecting group during a total synthesis of taxol and later as a direct provider of the crucial benzoate. As shown in Scheme 2, this method was readily reduced to practice. Treatment of 4 with phosgene in freshly distilled pyridine provided the desired carbonate, 5, in good yield. Simple addition of an excess of phenyllithium to a THF solution of this carbonate at −78° C. gave the benzoate as the single product. Acylation under standard conditions gave the enone 7. We have shown that protection of the C10 hydroxyl group is unnecessary and that if the C10 acetyl compound is subjected to this protocol partial deacylation of the 10-position occurs. This result leads us to expect easy access to a variety of C2 esters, a class of derivatives which was previously inaccessible and may prove very important given that moietie's importance in taxols SAR. A series of these proposed derivatives is also given in Scheme 2.

Scheme 2:
Regioselective installation of the 2-benzoyl group of taxol and taxotere.

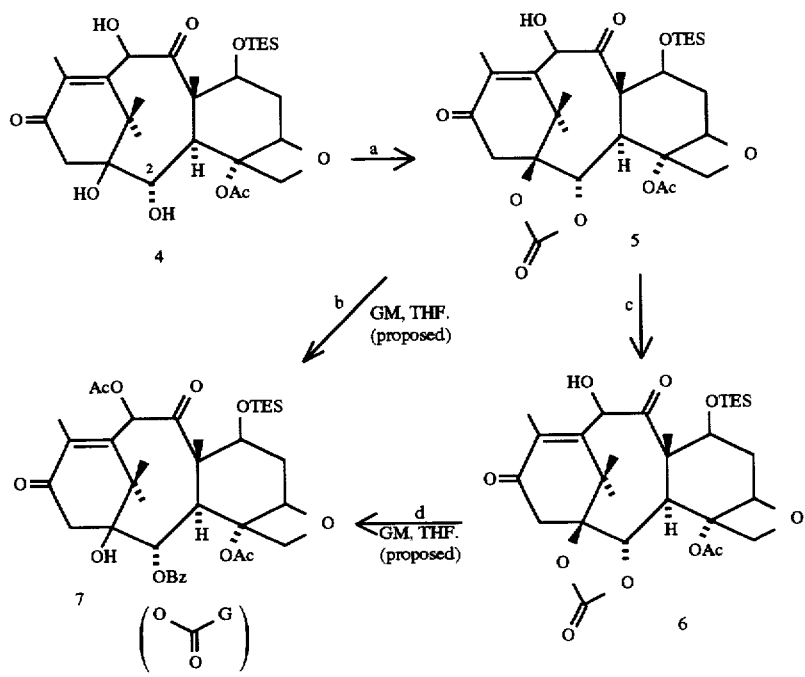

-continued
Scheme 2:
Regioselective installation of the 2-benzoyl group of taxol and taxotere.

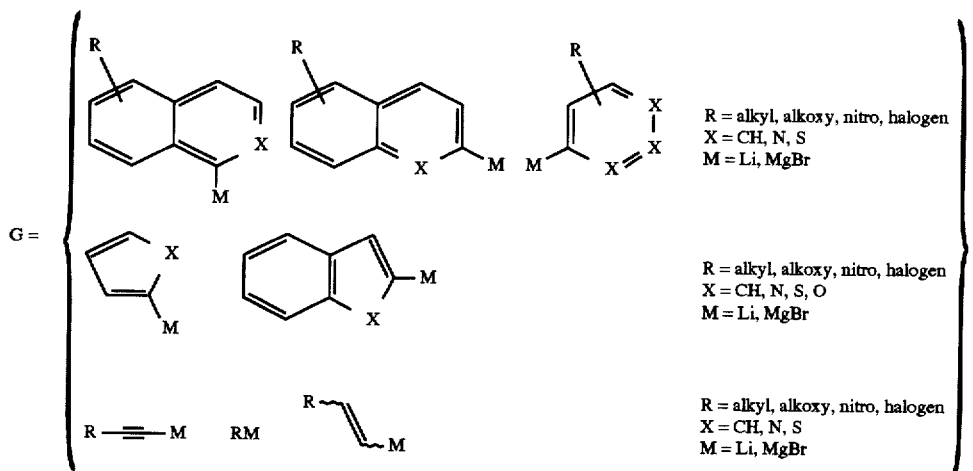

Reagents and conditions:
(a) COCl$_2$ (2eq.), pyridine, 25° C., 30 min., 80%;
(b) PhLi, THF, −78° C.,15 min.; then Ac$_2$O, DMAP, CH$_2$Cl$_2$ ,25° C., 1 h. 70% overall;
(c) Ac$_2$O, DMAP, CH$_2$Cl$_2$, 25° C., 2 h. 85%;
(d) PhLi, THF, −78° C., 15 min.; then Ac$_2$O, DMAP, CH$_2$Cl$_2$ 25° C., 1 h. 65 % overall.
(DMAP = N,N-dimethyl-4-aminopyridine; THF = tetrahydrofuran.)

Another important step in our total synthesis of taxol is the introduction of the oxygenation at the C13 position. As shown in Scheme 3, we employed a two step radical deoxygenation of 2 to give the C13 deoxy compound 8 as an inseparable mixture of tri- and tetra- substituted alkenes. Deprotection/reprotection according to our protocol described above is expected to give rise to the carbonate 9. This material should be readily converted to 6 by chromium mediated allylic oxidation.

Scheme 3:
Deoxygenation and reoxygenation at the 13 position.

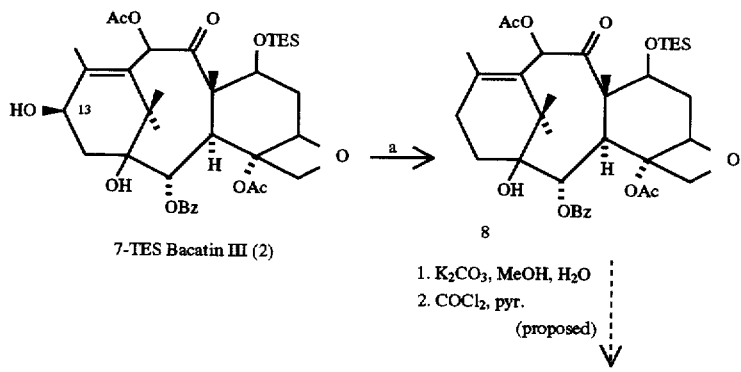

7-TES Bacatin III (2)

8

1. K$_2$CO$_3$, MeOH, H$_2$O
2. COCl$_2$, pyr.

(proposed)

-continued
Scheme 3:
Deoxygenation and reoxygenation at the 13 position.

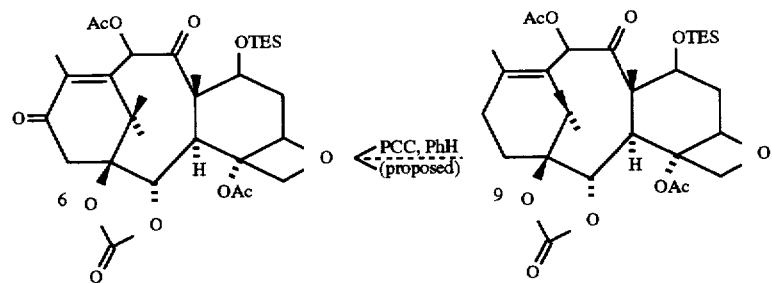

Reagents and conditions:
(a) (imidazole)₂C(S), DMAP, THF, 65° C., 48 h; then Bu₃SnH, AIBN, toluene, 90° C., 20 min, 40% overall.
{AIBN = azodiisobutylnitrile.}

Conversion of 7 back to taxol proceeded according to literature precedent. Acylation at the C10 position smoothly gave the expected enone acetate. Treatment of this material with sodium borohydride gave, with exclusive regio and stereo chemistry, the correct C13 alcohol. Introduction of the protected side chain, followed by deprotection should give taxol 1.

Scheme 4:
Conversion of 7 to taxol (1) and taxotere.

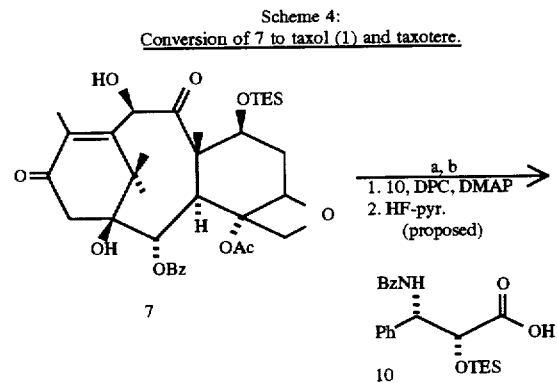

-continued
Scheme 4:
Conversion of 7 to taxol (1) and taxotere.

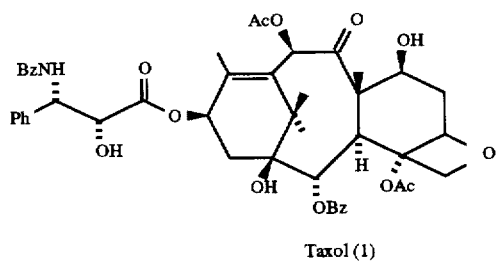

Taxol (1)

Reagents and conditions:
(a) Ac₂O (10 eq.), DMAP (15 eq.), CH₂Cl₂, 25° C., 4 h, 90%;
(b) NaBH₄, MeOH, 25° C., 3 h., 83%.

Since our synthetic strategy for taxol centers around the reductive coupling of a dialdehyde to produce the C9–C10 bond, we undertook studies aimed at oxidatively cleaving this bond. Initial attempts with lead tetraacetate on both taxol (1) and 10-deacetyl baccatin III (3) failed to produce cleavage products. As shown in Scheme 5, the major product in the case of 3 was that of oxidation at the C13 position. Similar studies on the enone 6, failed, with a variety of reagents, to produce any cleavage products.

Scheme 5:
Attempts to oxidatively cleave the C9-C10 bond.

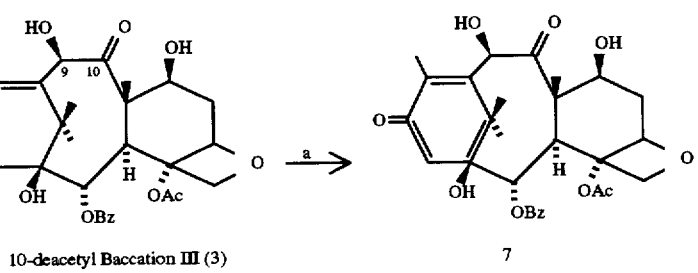

10-deacetyl Baccatin III (3)        7

-continued
Scheme 5:
Attempts to oxidatively cleave the C9-C10 bond.

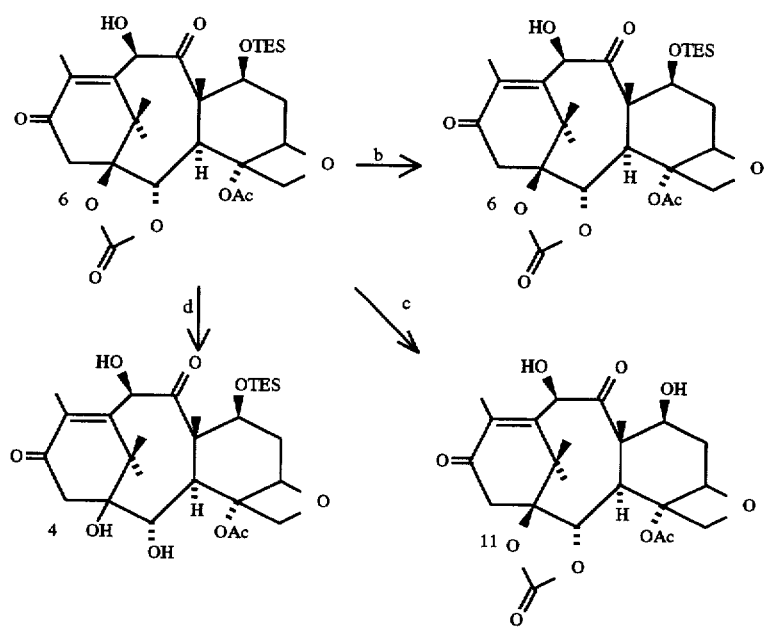

Reagents and conditions:
(a) Pb(OAc)$_4$ (15 eq.) 2:1 MeOH:benzene, 50° C., 3 h. 20%;
(b) Pb(OAc)$_4$ (15 eq.), 2:1 MeOH:benzene, 50° C., 3 h., no reaction;
(c) NaIO$_4$, 1:1 MeOH:H$_2$O, 25° C., 8 d., 85%;
(d) H$_2$O$_2$, NaOH, H$_2$O, MeOH, 0° C., 2 h., 80%.

Since our synthetic intermediates were not protected in exactly the same manner as our degradation products, we attempted to protect both the C1–C2 diol and the C7 hydroxyl group with a variety of moieties. As shown in Scheme 6, all attempts to introduce acetal or ketal groups at C1–C2 gave exclusive rearrangement to the cyclic ether 12. A similar ether has been proposed as the major side product during attempts to deprotect Baccatin III. As shown in Scheme 7, attempts to introduce other ethereal protecting groups than the TES resulted in either no reaction, exclusive epimerization at the C7 position, or opening of the oxetane via elimination.

Scheme 6:
Attempts to selectively protect the C1–C2 diol

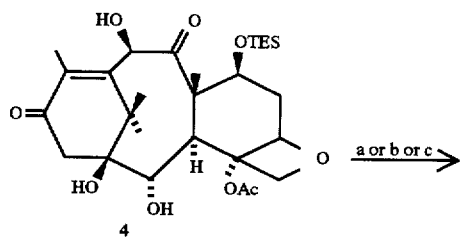

-continued
Scheme 6:
Attempts to selectively protect the C1–C2 diol

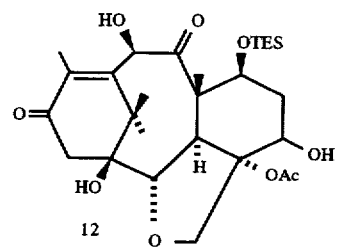

Reagents and Conditions:
(a) Me$_2$C(OMe)$_2$(2.0 eq.) CSA (cat.), CH$_2$Cl$_2$, 25° C., 1 h, 50%;
(b) Me$_2$CO, H$_2$SO$_4$, CH$_2$Cl$_2$ 25° C., 1 h, 50%;
(c) PhCH(OMe)$_2$, CSA (cat.), CH$_2$Cl$_2$, 25° C., 2 h, 50%.
(CSA = camphorsulfonic acid.)

Scheme 7:
Attempts to protect the 7-hydroxyl group.

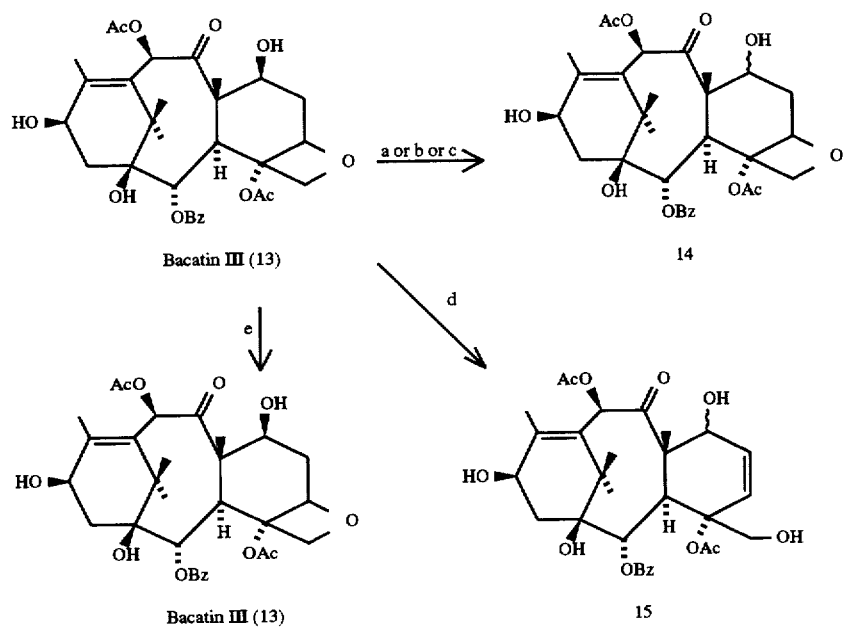

Reagents and conditions:
(a) TBSOTf (1.5 eq.), 2,6-lutidine (2 eq.), CH$_2$Cl$_2$, 0° C., 1 h, no reaction;
(b) TMSOTf (1.5 eq.), 2,6-lutidine (2 eq.) CH$_2$Cl$_2$, 0° C., 1 h, no reaction;
(c) BnBr (1.5 eq.), KH(excess), nBu$_4$NI (0.2 eq.), THF, 0° C., 1 h, epimerization at C7;
(d) BnOC(N)CCl$_3$ (1 eq.), F$_3$SO$_3$H (0.05 eq.), CH$_2$Cl$_2$, 25° C., 20 h;
(e) BnOTf (30 eq.), collidine (40 eq.), CH$_2$Cl$_2$, -80° C., 20 h, no reaction.

What is claimed is:

1. An improved method for producing key intermediate 4

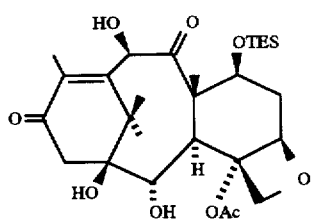

starting from a taxoid natural product, the improvement comprising the following steps:

Step A: providing the taxoid natural product; then

Step B: catalytically oxidating the taxoid natural product using Ley's ruthenium system to give a C13 ketone; and then Step C: hydrolyzing the product of said Step B under basic conditions to provide key intermediate 4.

2. A taxol analog having a C2 ester having the following structure:

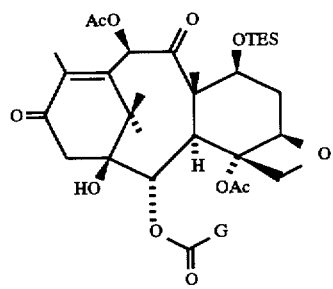

wherein G is selected from the group consisting of:

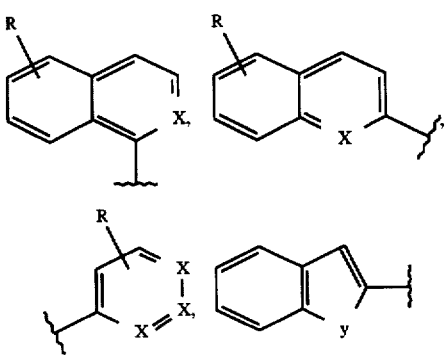

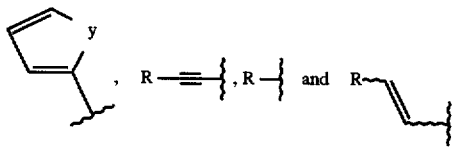
wherein:
R is a radical selected from the group consisting of alkyl, alkoxy, nitro, and halogen;
X is a radical selected from the group consisting of CH, and N; and
Y is a radical selected from the group consisting of CH, N, S, and O.
* * * * *